United States Patent [19]

Kiyomiya et al.

[11] Patent Number: 4,883,897
[45] Date of Patent: Nov. 28, 1989

[54] PROCESS FOR PRODUCING 2,6-DICHLOROBENZONITRILE

[75] Inventors: Yutaka Kiyomiya, Fujisawa; Yasumasa Yamaguchi; Masahiro Ushigome, both of Yokohama; Hiroshi Murata, Tokyo, all of Japan

[73] Assignee: Nitto Chemical Industry Co., Ltd., Tokyo, Japan

[21] Appl. No.: 135,353

[22] Filed: Dec. 21, 1987

[30] Foreign Application Priority Data

Dec. 19, 1986 [JP] Japan .................. 61-303363
Dec. 19, 1986 [JP] Japan .................. 61-303364

[51] Int. Cl.$^4$ .................. C07C 120/14; C07C 120/00; C07C 121/52
[52] U.S. Cl. .................. 558/327; 558/328
[58] Field of Search .................. 558/327, 328

[56] References Cited

U.S. PATENT DOCUMENTS

| | | | |
|---|---|---|---|
| 3,079,422 | 2/1963 | Pasky .................. | 558/327 |
| 3,341,565 | 9/1967 | Hartstra et al. .................. | 260/465 |
| 3,462,476 | 8/1969 | O'Donnell et al. .................. | 260/465 |
| 4,070,393 | 1/1978 | Angstadt et al. .................. | 558/327 X |
| 4,124,631 | 11/1978 | Hayami et al. .................. | 558/327 |
| 4,502,997 | 3/1985 | Tsao .................. | 558/327 |
| 4,582,647 | 4/1986 | Bayerl et al. .................. | 558/327 |

FOREIGN PATENT DOCUMENTS

| | | | |
|---|---|---|---|
| 619842 | 5/1961 | Canada .................. | 558/327 |
| 0158928 | 10/1985 | European Pat. Off. . | |
| 645754 | 11/1950 | United Kingdom .................. | 558/327 |

OTHER PUBLICATIONS

Japanese Patent Publication B-42-10214 (no date given).
Yukigosei Kagaku (Chemistry of Organic Synthesis) vol. 26, No. 3, (1968).
Hydrocarbon Processing—103, Feb. (1976) pp. 103–106.

*Primary Examiner*—Joseph Paul Brust
*Attorney, Agent, or Firm*—Cushman, Darby & Cushman

[57] ABSTRACT

A process for producing 2,6-dichlorobenzonitrile by ammoxidation comprising contacting a starting gas consisting of 2,6-dichlorotoluene, air and ammonia, which comprises carrying out this reaction under the following conditions:

(a) the concentration of 2,6-dichlorotoluene in the starting gas is 2.6 mole % or more.

(b) the reactor effluent gas is contacting with water to cool to a temperature in the range of 50° to 90° C., whereby 2,6-dichlorobenzonitrile in the reactor effluent gas is collected as a slurry in which solidified 2,6-dichlorobenzonitrile is dispersed in water, and 2,6-dichlorobenzonitrile is obtained from the slurry, and (c) the cooled reactor effluent gas from which 2,6-dichlorobenzonitrile has been removed is contacted with water again to cool to a temperature in the range of 0° to 40° C., whereby unreacted 2,6-dichlorotoluene in the gas is collected as a dispersion in which it is dispersed in water and 2,6-dichlorotoluene is recovered from the dispersion.

Also, there is disclosed a process for purifying 2,6-dichlorobenzonitrile obtained by subjecting 2,6-dichlorotoluene to ammoxidation, which comprises subjecting the 2,6-dichlorobenzonitrile to solid-liquid separation procedure in a molten state.

2 Claims, No Drawings

PROCESS FOR PRODUCING 2,6-DICHLOROBENZONITRILE

BACKGROUND OF THE INVENTION

1. Field of the Invention

The present invention relates to a method for collecting 2,6-dichlorobenzonitrile obtained by ammoxidation of 2,6-dichlorotoluene and a process for purifying the same.

2. Prior Art 2,6-dichlorobenzonitrile is very important in industry not only as a herbicide but also as a starting material of insecticides in recent years. This compound is usually produced by ammoxidation process of 2,6-dichlorotoluene, that is, a process in which 2,6-dichlorotoluene is subjected to catalystic reaction with oxygen molecule in the presence of ammonia.

One of such processes is disclosed in U.S. Pat. No. 4,582,647.

That is, above-mentioned U.S. Patent discloses a process for producing pure dichlorobenzonitrile by ammoxidation of 2,6-dichlorotoluene using a catalyst containing vanadium-molybdenum oxide, which is characterized by conducting the reaction by a fluidized bed method and spraying water into the reaction gas effluent out of the fluidized bed reactor.

This process, however, lacks consideration on recovery and utilization of unreacted 2,6-dichlorotoluene containing in the reactor effluent gas.

By this process, a large amount of nitrogen gas such as 3.5 to 7.7 times (Examples 1 to 9) of air is added to the starting gases in the reactors (Therefore, the concentration of the 2,6-dichlorotoluene in the starting gases is 1.93 to 2.03 mole %). Addition of such a large amount of nitrogen is disadvantageous in not only increase of amount of heat required for preheating the starting gas and cooling the reactor effluent gas but also difficulty in recovery of the unreacted 2,6-dichlorotoluene by cooling the reaction gas. Also, this method is disadvantageous in a low yield such as 60 to 72% (in Examples 1 to 9 of above-mentioned U.S. Patent) of 2,6-dichlorobenzonitrile obtained.

Though this process seems advantageous because recrystallization from a solvent is not necessary, thus obtained "pure" 2,6-dichlorobenzonitrile contains the catalyst and/or heavy metallic compounds derived from materials of the apparatus very much, so it has problems in its use according to what the present inventors know. It is understood that the heavy metallic compounds derived from the materials of the apparatus are due to corrosion of the apparatus by ammonium chloride inevitably formed as a by-product because the ammoxidation of 2,6-dichlorotoluene is carried out at a relatively high temperature. Though the problems of these heavy metallic compounds may be solved by filtration of the solution of 2,6-dichlorobenzonitrile and recrystallization, this process even has problems in recovery of the solvent used.

SUMMARY OF THE INVENTION

An aspect of the present invention is directed to a process of 2,6-dichlorobenzonitrile comprising subjecting 2,6-dichlorotoluene to ammoxidation in the presence of a catalyst having a metallic oxide on a carrier, in which the reaction is carried out without addition of nitrogen gas as dilution gas to the starting gas, highly pure 2,6-dichlorobenzonitrile is produced in a high yield and unreacted 2,6-dichlorotoluene is recovered.

Another aspect of the present invention is directed to a purification process in which 2,6-dichlorobenzonitrile produced by subjecting 2,6-dichlorotoluene to ammoxidation in the presence of a catalyst having a metallic oxide on a carrier is purified to decrease the contents of the catalyst and the heavy metallic compounds without use of a solvent, recovery of which entailes enormous cost.

According to the present invention, there is provided a process for producing 2,6-dichlorobenzonitrile comprises contacting a starting gas consisting of 2,6-dichlorotoluene, air and ammonia with a fluidized bed catalyst in which a metallic oxide is carried on a carrier, which is characterized by carrying out this reaction under the following conditions:

(a) the concentration of 2,6-dichlorotoluene in the starting gas is 2.6 mole % or more.

(b) the reactor effluent gas is contacted with water to cool to a temperature in the range of 50° to 90° C., whereby 2,6-dichlorobenzonitrile in the reactor effluent gas is collected as a slurry in which solidified 2,6-dichlorobenzonitrile is dispersed in water, and 2,6-dichlorobenzonitrile is obtained from the slurry, and (c) the cooled reactor effluent gas from which 2,6-dichlorobenzonitrile has been removed is contacted with water again to cool to a temperature in the range of 0° to 40° C., whereby unreacted 2,6-dichlorotoluene in the gas is collected as a dispersion in which it is dispersed in water and 2,6-dichlorotoluene is recovered from the dispersion.

According to the present invention, there is provided a process for purifying 2,6-dichlorobenzonitrile comprising purifying 2,6-dichlbrobenzonitrile obtained by subjecting 2,6-dichlorotoluene to ammoxidation in the presence of a catalyst in which a metallic oxide is carried on a carrier, which is characterized by subjecting the 2,6-dichlorobenzonitrile to solid-liquid separation procedure in a molten state.

DETAILED DESCRIPTION OF THE INVENTION

Ammoxidation

Ammoxidation of 2,6-dichlorotoluene is a known technique and the known technique can be used in the present invention so long as it is not contradictory to the present invention.

According to the present invention, the reaction is carried out using a fluidized bed catalyst. As obvious from the concentration of 2,6-dichlorotoluene in the starting gas of 2.6 mole % or more, preferably 3 mole % or more, the starting gas is substantially consisting of 2,6-dichlorotoluene air and ammonia, and hence, it contains no diluent such as nitrogen gas, steam or the like in fact.

As the catalyst of ammoxidation of 2,6-dichlorotoluene, there may be used, for example, a catalyst in which alumina or silica carries oxides of heavy metals selected from the group consisting of vanadium, chromium, molybdenum, antimony and iron. For example, there may be used the catalysts described in Japanese Patent Publication Nos. 7,902/67 and 5,386/68.

As the catalyst used for producing 2,6-dichlorobenzonitrile, there may be used a catalyst obtained by preparing a base catalyst by calcining metallic oxide composition essentially containing antimony, at least one element selected from the group consisting of iron, cobalt, nickel, chromium, copper, titanium, thorium and cerium, and silica at 500° to 950° C., impregnating the base catalyst with a solution containing a vanadium compound having a proportion of the impregnating vanadium component to antimony component in the base catalyst (V/Sb, atomic ratio) adjusted to 0.005 to 5, drying it and then calcining it at a temperature of 300° to 800° C.

Explanation will be provided in more detail below.

First, a base catalyst essentially containing antimony, at least one element selected from the group consisting of iron, cobalt, nickel, tin, uranium, chromium, copper, titanium, thorium and cerium, and silica is produced. For this purpose, there may be used each process disclosed in Japanese Patent Publication No. 22,476/67, Japanese Patent Publication No. 18,722/72 (U.S. Pat. No. 3,657,155), Japanese Patent Publication No. 18,723/72 (U.S. Pat. No. 3,686,138), etc.

The base catalyst preferably has a composition represented by the experimental formula as follows:

$$Me_aSb_bX_cQ_dR_eS_fO_g(SiO_2)_h$$

wherein Me is at least one element selected from the group consisting of Fe, Co, Ni, Sn, U, Cr, Cu, Mn, Ti, Th and Ce, X is at least one element selected from the group consisting of V and Mo, Q is at least one element selected from the group consisting of Be, Mg, Ca, Sr, Ba, Y, La, Zr, Hf, W, Nb, Ta, Re, Ru, Os, Rh, Ir, Pd, Pt, Ag, Zn, Cd, Al, Ga, In, Ge and Pb, R is at least one element selected from the group consisting of B, P, Te, Bi, As and Se, S is at least one element selected from the group consisting of Li, Na, K, Rb, Cs and Tl, and annexed letters of a, b, c, d, e, f, g and h show atomic ratios and are respectively in the following ranges:

a=5-15,
b=5-100 (preferably 10-50),
c=0-15 (preferably 0.01-10),
d=0-20 (preferably 0.05-15),
e=0-10 (preferably 0.1-7),
f=0-5 (preferably 0.05-3) and
h=10-200 (preferably 20-150), and O represents oxygen atom and g shows number of oxygen atoms corresponding to oxide formed by combining with each component element.

Thus prepared base catalyst is impregnated with an aqueous solution of vanadium compound.

The vanadium compound used in preparation of the impregnating solution includes ammonium metavanadate, vanadyl oxalate, vanadyl sulfate, vanadyl phosphate, vanadyl acetylacetonate, vanadium-containing heteropoly acid, salts of the same or the like. Also, there may be used an aqueous hydrogen peroxide solution of vanadium oxide or vanadic acid (vanadate).

Impregnation can also be carried out simultaneously with additional components other than the vanadium compound. In this case, water soluble compounds of these components may be used. In the case of iron, cobalt, nickel, chromium, copper, manganese, cerium, lanthanum, zirconium, magnesium, calcium, strontium, barium, silver, zinc, cadmium, aluminum, gallium, germanium, lead or the like, the nitrate is preferably used. A salt thereof with an organic acid is also preferably used. In the case of lithium, sodium, potassium, rubidium or cesium, the hydroxide or the nitrate is preferably used. Boron is used as boric acid as it is or preferably in a state having a increased solubility by using glycerol, propylene glycol, tartaric acid, lactic acid, malic acid or the like. Phosphorus is preferably used as phosphoric acid. Bismuth is preferably used as the nitrate.

By dissolving the compound mentioned above in water, a solution containing vanadium, an element other than vanadium or both of vanadium and an element other than vanadium is prepared.

The base catalyst is impregnated with the solution of which volume is adjusted to a volume corresponding to the pore capacity of the base catalyst previously measured. If the amount of impregnating vanadium is too small, satisfactory activity can not be obtained while if it is too large, high activity can be obtained but selectivity of the intended product decreases. In the case of a fluidized bed catalyst, there are brought disadvantages such that adhesion of the catalyst increases and hence, fluidized condition deteriorates, resulting in lowered yield of the intended product.

The amount of vanadium to impregnate is preferable in the range regulated as follows. The proportion of the amount of vanadium component to impregnate to the amount of antimony component in the base catalyst, V/Sb (atomic ratio) is in the range of 0.005 to 5, preferably 0.01 to 2, more preferably 0.03 to 1.5.

Impregnation of the component other than vanadium besides may preferably be conducted as follows.

If the component other than vanadium is referred to as T, T is at least one element selected from the group consisting of Fe, Co, Ni, Cr, Cu, Mn, Ce, La, Zr, Mg, Ca, Sr, Ba, Ag, Zn, Cd, Al, Ga, Ge, Pb, Li, Na, K, Rb, Cs, B, P and Bi, and T/V (atomic ratio) is preferably in the range of 0.01 to 10, particularly in the range of 0.05 to 5.

Though it is economical that the impregnation is carried out once by preparing a uniform solution containing the required amount of the component, procedures of impregnation and drying (if necessary, and calcination) may be repeated several times by using an impregnating solution having a low concentration, if necessary. Also, impregnating solutions having different kinds or amounts of the components are prepared and the procedures of impregnation and drying (if necessary and calcination) may be carried out in turn. When the impregnating amount is relatively large, the plural time impregnation is recommended.

Thus, the base catalyst is impregnated with an aqueous solution of vanadium or both of vanadium and the other component element, then dried and calcined at a temperature of 300° to 800° C. to obtain a complete catalyst.

The catalyst thus obtained usually has the preferable following composition:

$$Me_iSb_jV_kMo_lQ_mR_nS_oO_p(SiO_2)_q$$

wherein Me is at least one element selected from the group consisting of Fe, Co, Ni, Sn, U, Cr, Cu, Mn, Ti, Th and Ce, Q is at least one element selected from the group consisting of Be, Mg, Ca, Sr, Ba, Y, La, Zr, Hf, W, Nb, Ta, Re, Ru, Os, Rh, Ir, Pd, Pt, Ag, Zn, Cd, Al, Ga, In, Ge and Pb, R is at least one element selected from the group consisting of B, P, Te, Bi, As and Se, S is at least one element selected from the group consisting of Li, Na, K, Rb, Cs and Th, and annexed letters of i, j, k, l, m, n, o, p and q show atomic ratios and respectively in the following ranges:

i=5-15
j=5-100 (preferably 10-50), k=0.01–15 (preferably 0.1–10),
l=0–10 (preferably 0.05–7),
m=0–20 (preferably 0.05–15),
n=0–10 (preferably 0.1–7),
o=0–5 (preferably 0.05–3) and
q=10–200 (preferably 20–150),
and O represents oxygen atom and p shows number of oxygen atoms corresponding to oxide formed by combining with each component element.

REFERENTIAL EXAMPLE 1

A catalyst having an experimental formula of $Fe_{8.8}Cu_{3.2}Sb_{20}V_2O_{61.4}(SiO_2)_{48}$ was prepared as follows.

With 750 ml of pure water is mixed 600 ml of an aqueous nitric acid solution having a specific gravity of 1.38. The resulting solution is heated. Thereto is added 73.0 g of electrolylic iron powder little by little. Complete dissolving is confirmed. Thereto is added 115 g of copper nitrate. To the resulting solution containing iron and copper is added 1,785 g of silica sol. To the resulting solution is added 433 g of antimony trioxide. To the resulting slurry is added a 15% by aqueous ammonia solution little by little to adjust the pH to 2.5. The resulting slurry is heated under reflux at 95° C. for 5 hours, then subjected to spray drying in a usual manner, and calcined at 200° C. for 4 hours, then at 400° C. for 4 hours, and finally at 850° C. for 4 hours to give a base catalyst having a composition of $Fe_{8.8}Cu_{3.2}Sb_{20}O_{70.5}$—$(SiO_2)_{40}$.

On the other hand, 27.0 g of vanadium pentaoxide is suspended in 200 ml of pure water. The resulting suspension is heated to 90° C. Oxalic acid is added thereto little by little and dissolved therein. The base catalyst containing iron, antimony, copper and silica prepared above is impregnated with the resulting solution containing vanadium and calcined at 200° C. for 4 hours and then at 450° C. for 4 hours. The proportion of the amount of vanadium component in the impregnating solution to the amount of antimony component, V/Sb (atomic ratio) is 0.1.

REFERENTIAL EXAMPLE 2

A catalyst having an experimental formula of $Fe_{10}Cu_{3.2}Sb_{20}V_4Mo_{0.56}W_{10.08}Te_{1.36}O_{72.8}(SiO_2)_{56}$ was prepared in the same manner as in Referential Example 1.

The base catalyst having a composition of $Fe_{10}Cu_{3.2}Sb_{20}V_{0.16}Mo_{0.56}W_{0.08}Te_{1.36}O_{63.2}(SiO_2)_{56}$ was impregnated with a vanadium component. The atomic ratio of V/Sb is 0.192.

Though the conversion is important in the ammoxidation of 2,6-dichlorotoluene in a catalyst fluidized bed reactor, the heightened conversion has a tendency that the selectivity of 2,6-dichlorobenzonitrile lowers greatly. Therefore, the conversion is suitably in the range of from 80% to 97%, preferably from 85% to 95%. When the conversion exceeds the upper limit, the selectivity of 2,6-dichlorobenzonitrile decreases and the total yield of 2,6-dichlorobenzonitrile decreases. When the conversion is lower than the lower limit, the amount of 2,6-dichlorotoluene contained in the 2,6-dichlorobenzonitrile obtained in the first collecting column increases. In order to prevent this increase, it is necessary to lift the temperature in the first collecting column and as a result, the amount of water evaporated increases. This is econimically disadvantageous.

For regulating the conversion in the reactor within the range mentioned above, the contact time with the catalyst is suitably in the range of from 2 seconds to 20 seconds, preferably from 3 seconds to 10 seconds.

The reaction temperature is suitably in the range of from 300° C. to 450° C., preferably from 350° C. to 400° C. When the reaction temperature exceeds 450° C., decomposition of 2,6-dichlorobenzonitrile increases and the reaction yield of it decreases greatly.

In the reaction, the molar ratio of ammonia to 2,6-dichlorotoluene is 1 to about 10, preferably 2 to about 7, and the molar ratio of oxygen to 2,6-dichlorotoluene is 2 to about 6, preferably 3 to about 5.

Cooling of Reactor Effluent Gas

According to the present invention, the reaction gas effluent out of the reactor is cooled in two steps by using two cooling apparatus connected in series and contacting the reactor effluent gas with water in each cooling apparatus. In the first cooling apparatus, the reactor effluent gas is cooled to a temperature of 50° C. to 90° C. When the temperature of the gas is lowered, content of 2,6-dichlorotoluene in the 2,6-dichlorobenzonitrile collected increases while when the temperature of the gas is heightened, the content of 2,6-dichlorotoluene collected decreases. Therefore, depending on the concentration of the unreacted 2,6-dichlorotoluene the temperature of the gas out of the first cooling apparatus is selected from the temperature between 50° C. and 90° C. so as to regulate the concentration of 2,6-dichlorotoluene incorporated in the collected 2,6dichlorobenzonitrile to 1% or less, preferably 0.5% or less.

The 2,6-dichlorotoluene condensed in the first cooling apparatus is mainly incorporated into 2,6-dichlorobenzonitrile and dissolved very slightly in water.

By cooling the reactor effluent gas to 0° C. to 45° C. in the second cooling apparatus, 2,6-dichlorotoluene uncondensed in the first cooling apparatus is recovered. The 2,6-dichlorotoluene recovered in the second cooling apparatus is dispersed in water and can be separated from the water by liquid-liquid separation procedure. Thus recovered 2,6-dichlorotoluene can be supplied into the reactor for ammoxidation as a part of the feed 2,6-dichlorotoluene.

As the cooling apparatus, any known vapor-liquid contacting apparatus can be used and there may be used a spray column in which water is sprayed, a cyclone scrubber, a Venturi scrubber, a wet wall column, a packed column and the like.

In the cooling apparatus, water is circulated and the water is cooled by means of a heat exchanger for adjusting it to the required temperature.

In order to prevent accumulation of impurities in the water and to obtain 2,6-dichlorobenzonitrile free from impurities, it is necessary to take out a part of the circulating water and newly supply with water.

The slurry of 2,6-dichlorobenzonitrile obtained in the first cooling apparatus is subjected to solid-liquid separation in a known method using a filter, a centrifugal separator or the like to separate 2,6-dichlorobenzonitrile from the water. If necessary, by washing with water, 2,6-dichlorobenzonitrile containing 2,6-dichlorotoluene in a content of 1% or less can be obtained.

If necessary, the obtained 2,6-dichlorobenzonitrile can be dried in a known method.

The crude 2,6-dichlorobenzonitrile obtained in the above-mentioned process, in the process disclosed in Japanese Patent Application Kokai (Laid-Open) No. 228,452/85, or in known processes is heated and molten in a melting apparatus. The temperature of the molten matter is suitably in the range of from about 145° C. to about 200° C., particularly preferably from 150° C. to 170° C. The melting can be carried out in a non-oxidizing atmosphere, for example, in nitrogen gas atmosphere. Wet 2,6-dichlorobenzonitrile may be used after it has been dried.

For the solid-liquid separation procedure, any means can be used if it attains this object. One means is centrifugal separation and one of the other means is filtration. The filtration is usually preferable.

The filtration can be carried out by using a filter medium having a suitable pore opening or filtration precision. The filtration precision of the filter medium to be used is in the range of about $0.2\mu$ to about $100\mu$, preferably about $1\mu$ to about $10\mu$. The terms "filtration precision" used herein means particle diameter in terms of $\mu$m of the largest particle remained in the filtrate after filtration.

The filter medium having such filtration precision includes various materials such as, for exmaple, filter papers, woven wires, sintered products, heatresistant membranes such as those made of polytetrafluoroethylene, etc. These can also be used together with a filtration adjuvant commonly used for solid liquid separation, for example diatomaceous earth, carbon block, etc.

Though the filtration can be carried out batchwise, automatically batchwise or continuously, pressure filtration is suitable because the amount of 2,6-dichlorobenzonitrile lost by evaporation is small.

The filtrate consisting of purified 2,6-dichlorobenzonitrile is solidified by cooling. It is preferable to obtain the solidified product as flakes by using a flaking machine. The resulting flakes of 2,6-dichlorobenzonitrile are pulverized, if necessary, to give a product.

The present invention will be described referring to Examples, which are of course not by way of limitation.

First, a process for producing 2,6-dichlorobenzonitrile, which is an aspect of the present invention is explained.

In Examples and Comparative Examples conversion and total yield are defined as follows:

$$\text{Conversion (\%)} = \frac{\text{Amount by mole of reacted DCT}}{\text{Amount by mole of DCT supplied into reactor}} \times 100$$

$$\text{Total yield (\%)} = \frac{\text{Amount by mole of DBN obtained by reacting, collecting and solid-liquid separating}}{\text{Amount by mole of DCT supplied into reactor} - \text{mole of DCT recovered}} \times 100$$

$$\text{Selectivity (\%)} = \frac{\text{Amount by mole of produced DBN}}{\text{Amount by mole of reacted DCT}} \times 100$$

DCT: 2,6-Dichlorotoluene

DBN: 2,6-Dichlorobenzonitrile

EXAMPLE 1

A stainless steel fluidized bed reactor having an inner diameter of 81 mm (about 3 inches) and a height of about 4 m was packed with 7 kg of fluidized bed catalyst in which 1.9% of vanadium oxide, 3.0% of chromium oxide, 9.7% of iron oxide and 35.5% of antimony oxide were carried on silica. The reactor was charged with 2,6-dichlorotoluene, ammonia and air, and the reaction was carried out.

The reaction temperature was about 360° C., and the contact time of the reaction gas with the catalyst was about 7.5 seconds. The rates of 2,6-dichlorotoluene, ammonia and air supplied into the reactor were 3.0 moles/hour, 15 moles/hour and 50 moles/hour, respectively, and the molar ratios of ammonia to 2,6-dichlorotoluene and of oxygen to 2,6-dichlorotoluene were 5.0 and 3.5, respectively.

The reactor effluent gas was introduced into a stainless steel cooling column having an inner diameter of about 81 mm (about 3 inches) and a height of 2 m and contacted with circulating water at the flow rate of 1 m³/hour to be cooled to 70° C. The temperature of the circulating water was regulated in a heat exchanger provided in circulation line by cooling with water. The reactor effluent gas cooled in the first cooling column was introduced into a second cooling column of which detail is similar to the first cooling column and contacted with water cooled with brine solution to be cooled to 10° C.

The first cooling column was replenished with water at the rate of 1 liter/hour. The resulting slurry of 2,6-dichlorobenzonitrile was centrifuged. A part of the separated mother liquor was taken out and the rest was returned into the first cooling column.

A part of the circulating water was drawn out of the second cooling column and subjected to liquid-liquid separation to recover 2,6-dichlorotoluene, which was then returned to the reactor as a part of the starting material. Excess water was taken out and the rest was returned into the second cooling column.

The content of 2,6-dichlorotoluene in the resulting 2,6-dichlorobenzonitrile was 0.1%, and the total yield of 2,6-dichlorobenzonitrile was 81%. The conversion of 2,6-dichlorotoluene was 90%.

EXAMPLE 2

Trial run was carried out under the same conditions as in Example 1, except that the following conditions were used.

Amount of catalyst packed: about 5.8 kg.

Amounts of starting materials charged:
2,6-Dichlorotoluene: 3 moles/hour
Ammonia: 21 moles/hour
Air: 71 moles/hour The result of the trial is as shown in Table 1.

EXAMPLE 3

Trial run was carried out under the same conditions as in Example 1, except that the following conditions were used.

Amount of catalyst packed: about 9.1 kg.

Amounts of starting materials charged:
2,6-Dichlorotoluene: 3 moles/hour
Ammonia: 12 moles/hour
Air: 57 moles/hour The result of the trial is as shown in Table 1.

COMPARATIVE EXAMPLE 1

Trial run was carried out under the same conditions as in Example 1, except that only first cooling column was used and cooling was effected at 40° C.

As shown in Table 1, it is understood from the result o the trial that the yield of 2,6-dichlorobenzonitrile is low as 76% and the content of 2,6-dichlorotoluene in the resulting 2,6-dichlorobenzonitrile is 4% so that a purification step such as recrystalization from a solvent or the like is required in order to decrease the content to 1% or less.

EXAMPLE 4

Trial run was carried out under the same conditions as in Example 1, except that the cooling in the first cooling column was effected at 50° C.

The result of the trial is as shown in Table 1.

COMPARATIVE EXAMPLE 2

Trial run was carried out under the same conditions as in Example 3, except that the amount of catalyst packed was 7 kg, only the first cooling column was used and cooling was effected at 25° C.

The result of the trial is as shown in Table 1.

COMPARATIVE EXAMPLE 3

Trial run was carried out under the same conditions as in Example 3, except that only first cooling column was used and cooling was effected at 25° C.

The result of the trial is as shown in Table 1.

machine. The separated wet 2,6-dichlorobenzonitrile was dried in a dryer.

(2) Purification of the 2,6-dichlorobenzonitrile

The obtained 2,6-dichlorobenzonitrile was molten at 155° C., and the molten liquid was filtered through a filter paper (filtration precision: about 5 μm, Toyo Roshi filter paper for production). The filtrate was solidified by cooling and then pulverized to obtain powdered 2,6-dichlorobenzonitrile.

Concentration of heavy metals in the unfiltered dried product and the molten and filtered product were measured by atomic-absorption spectroscopy. The results are as follows.

|  | Heavy metals in the 2,6-dichlorobenzonitrile (ppm) | | | | |
| --- | --- | --- | --- | --- | --- |
|  | Cr | Fe | Sb | Ni | V |
| Dried product (without filtration) | 34 | 60 | 43 | 3.8 | 2 |
| molten and filtered product of the present invention | 0.7 | 1.0 | 0.8 | 0.4 | 0.2 |

TABLE 1

|  | Contact time (sec.) | Molar ratio NH$_3$ | Molar ratio O$_2$ | Concentration of DCT in reaction starting gas (mole %) | Conversion (%) | Temperature in cooling apparatus (°C.) First step | Temperature in cooling apparatus (°C.) Second step | Total yield DBN of (%) | Content of DCT in DBN (%) |
| --- | --- | --- | --- | --- | --- | --- | --- | --- | --- |
| Example 1 | about 7.5 | 5.0 | 3.5 | 4.4 | 90 | 70 | 10 | 81 | 0.1 |
| Example 2 | about 4.4 | 7.0 | 5.0 | 3.2 | 85 | 80 | 10 | 81 | 0.1 |
| Example 3 | about 9.2 | 4.0 | 4.0 | 4.2 | 95 | 60 | 10 | 81 | 0.05 |
| Example 4 | about 7.5 | 5.0 | 3.5 | 4.4 | 90 | 50 | 10 | 81 | 0.2 |
| Comparative Example 1 | about 7.5 | 5.0 | 3.5 | 4.4 | 90 | 40 | — | 76 | 4 |
| Comparative Example 2 | about 7.1 | 4.0 | 4.0 | 4.2 | 90 | 25 | — | 76 | 9 |
| Comparative Example 3 | about 9.2 | 4.0 | 4.0 | 4.2 | 95 | 25 | — | 78 | 3 |

As mentioned above, according to the present invention, by carrying out the cooling process by contacting the reaction gas obtained by ammoxidation with water in two steps, 2,6-dichlorobenzonitrile is collected in the first step and 2,6-dichlorotoluene is recovered in the second step, whereby 2,6-dichlorobenzonitrile containing 1% or less of 2,6-dichlorotoluene can be obtained without use of nitrogen gas for diluting the reaction gas.

Next, purification process which is another aspect of the present invention is explained.

EXAMPLE 5

(1) Production of 2,6-dichlorobenzonitrile

A stainless steel fluidized bed reactor was packed with a catalyst prepared according to above-mentioned Referential Example 1 having a composition represented by the experimental formula of Fe$_{10}$Sb$_{20}$V$_{1.7}$Cr$_{3.2}$O$_{54.4}$(SiO$_2$)$_{68}$ in which 1.9% of vanadium oxide, 3.0% of chromium oxide, 9.7% of iron oxide and 35.5% of antimony oxide were carried on silica. The reactor was charged with a mixed gas consisting of 2,6-dichlorotoluene, ammonia and air. The molar ratio of ammonia to 2,6-dichlorotoluene was 5.0 and molar ratio of oxygen to 2,6-dichlorotoluene was 3.5. The temperature in the reaction zone was about 360° C. and the contact time of the feed gas with the catalyst was about 7.5 seconds. The reactor effluent gas was cooled with circulating water cooled in heat exchanger to about 70° C. The resulting slurry was separated by a centrifugal

EXAMPLE 6

The 2,6-dichlorobenzonitrile produced in the same manner as in Example 5 was molten at 155° C. The resulting molten liquid was filtered through a membrane made of Teflon (manufactured by Nihon Milipore Co., Ltd., pore diameter: 5.0 μm). The filtrate was solidified by cooling, and pulverized to obtain powdered 2,6-dichlorobenzonitrile.

Concentrations of heavy metals in the unfiltered dried product and the molten and filtered product were measured by atomic-absorption spectroscopy. The results are as follows.

|  | Heavy metals in the 2,6-dichlorobenzonitrile (ppm) | | | | |
| --- | --- | --- | --- | --- | --- |
|  | Cr | Fe | Sb | Ni | V |
| Dried product (without filtration) | 26 | 95 | 50 | 9 | 4 |
| Product filtered through membrane of the present invention | 0.4 | 2.5 | 1.2 | 0.3 | 0.5 |

EXAMPLE 7

The 2,6-dichlorobenzonitrile produced in the same manner as in Example 5 was molten at 155° C. The resulting molten liquid was filtered through a sintered metal filter (manufactured by SMC Co., Ltd., nominal filtration precision: 2 μm). The filtrate was solidified by cooling and pulverized to obtain powdered 2,6-dichlorobenzonitrile.

Concentration of heavy metals in the unfiltered dried product and the molten and filtered product were measured by atomic-absorption spectroscopy The results are as follows.

|  | Heavy metals in the 2,6-dichlorobenzonitrile (ppm) | | | | |
| --- | --- | --- | --- | --- | --- |
|  | Cr | Fe | Sb | Ni | V |
| Dried product (without filtration) | 19 | 87 | 26 | 4.9 | 4 |
| Product filtered through sintered metal filter of the present invention | 0.3 | 2.5 | 0.8 | 0.2 | 0.4 |

Heavy metallic compounds contained in the 2,6-dichlorobenzonitrile obtained in ammoxidation can be removed without use of any solvent, which costs so much in recovery or the like, only by melting and filtration.

Since the melting point of 2,6-dichlorobenzonitrile is high such as 144° C. to 145° C. and the crude 2,6-dichlorobenzonitrile obtained in ammoxidation contains heavy metallic compounds, when heated to a temperature of the melting point or higher it is anxious about troubles of decomposition, coloration and the like, however, the present inventors have found that such troubles are undetected.

It is understood as an unexpected phenomenon that heavy metallic compounds can be removed in the level of detectable by atomic-absorption spectroscopy in purification process by solid-liquid separation according to the present invention. That is, when molten 2,6-dichlorobenzonitrile is filtered through a filter paper having a small filtration precision, not only fragments of catalyst as solid contained in the 2,6-dichlorobenzonitrile but also the other heavy metallic compounds can be removed as brown segment to give 2,6-dichlorobenzonitrile with a low content of heavy metallic compounds.

What is claimed is:

1. A process for producing 2,6-dichlorobenzonitrile comprises contacting a starting gas consisting of 2,6-dichlorotoluene, air and ammonia with a fluidized bed a metallic oxide ammoxidation catalyst is carried on a carrier under the following conditions:
    (a) the concentration of 2,6-dichlorotoluene in the starting gas is 2.6 mole % or more,
    (b) the reactor effluent gas is contacted with water to cool to a temperature in the range of 50° to 90° C., whereby 2,6-dichlorobenzonitrile in the reaction product gas is collected as a slurry in which solidified 2,6-dichlorobenzonitrile is dispersed in water, and 2,6-dichlorobenzonitrile is obtained from the slurry, and
    (c) the cooled reactor effluent gas from which 2,6-dichlorobenzonitrile has been removed is contacted with water again to cool to a temperature in the range of 0° to 40° C., whereby unreacted 2,6-dichlorotoluene in the gas is collected as a dispersion in which it is dispersed in water and 2,6-dichlorotoluene is recovered from the dispersion.

2. A process for producing 2,6-dichlorobenzonitrile according to claim 1, wherein the process is carried out under the condition capable of meeting further at least one selected from the following ones:
    (a') the concentration of 2,6-dichlorotoluene in the starting gas is 3 mole % or more, and
    (d) the conversion of 2,6-dichlorotoluene in the ammoxidation ranges from 80 to 97%.

* * * * *